(12) United States Patent
Bischoff et al.

(10) Patent No.: US 12,127,980 B2
(45) Date of Patent: *Oct. 29, 2024

(54) CREATION OF CURVED CUTS IN THE INSIDE OF THE EYE CORNEA

(71) Applicant: CARL ZEISS MEDITEC AG, Jena (DE)

(72) Inventors: Mark Bischoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,367

(22) Filed: Feb. 27, 2023

(65) Prior Publication Data
US 2023/0277378 A1 Sep. 7, 2023

Related U.S. Application Data

(63) Continuation of application No. 17/037,441, filed on Sep. 29, 2020, now Pat. No. 11,602,458, which is a
(Continued)

(30) Foreign Application Priority Data

Mar. 14, 2013 (DE) ...................... 10 2013 204 496.8

(51) Int. Cl.
*A61F 9/008* (2006.01)
(52) U.S. Cl.
CPC ........ *A61F 9/00827* (2013.01); *A61F 9/0084* (2013.01); *A61F 2009/00872* (2013.01)
(58) Field of Classification Search
CPC .................................. A61F 9/008–2009/00897
See application file for complete search history.

(56) References Cited

U.S. PATENT DOCUMENTS 5,984,916 A 11/1999 Lai
9,545,340 B1 1/2017 Knox et al.
(Continued)

FOREIGN PATENT DOCUMENTS

DE 102 02 036 A1 7/2003
DE 10 2008 056 488 A1 5/2010
(Continued)

OTHER PUBLICATIONS

Shah, Rupal, et al., "Effect of scanning patterns on the results of femtosecond laser lenticule extraction refractive surgery," *J. Cataract Refract. Surg.*, vol. 37, pp. 1636-1647 (2011).
(Continued)

*Primary Examiner* — Jonathan T Kuo
(74) *Attorney, Agent, or Firm* — Christensen, Fonder, Dardi & Herbert PLLC

(57) ABSTRACT

A device for isolating a lenticle in the cornea of an eye. The device includes: a laser beam source to emit pulsed laser radiation having a pulse frequency of 1.2 MHz to 10 MHz, a pulse energy of 1 nJ to 200 nJ and a wavelength penetrating the cornea; a beam-forming unit having beam optics with an image field and that bundles pulsed laser radiation into a focus located inside the image field, and which has a maximum diameter of less than 3 μm; a beam-deflection unit shifting the focus in the cornea and inside the image field, the focus moving along a path when the image field is resting; and a control unit to control the source and the beam-forming unit to isolate the lenticle by specifying the path. The lenticle is delimited by a cut surface which is curved with regard to a front surface of the cornea.

20 Claims, 1 Drawing Sheet

Related U.S. Application Data continuation of application No. 14/774,677, filed as application No. PCT/EP2014/052167 on Feb. 4, 2014, now Pat. No. 10,893,979.

(56) References Cited

U.S. PATENT DOCUMENTS

| | | | |
|---|---|---|---|
| 10,893,979 B2 * | 1/2021 | Bischoff | A61F 9/0084 |
| 11,602,458 B2 * | 3/2023 | Bischoff | A61F 9/00827 |
| 2004/0243111 A1 | 12/2004 | Bendett et al. | |
| 2004/0243112 A1 | 12/2004 | Bendett et al. | |
| 2007/0179478 A1 * | 8/2007 | Dobschal | A61F 9/009 219/121.75 |
| 2007/0293851 A1 | 12/2007 | Muhlhoff et al. | |
| 2008/0269731 A1 | 10/2008 | Swinger et al. | |
| 2008/0319428 A1 | 12/2008 | Wiechmann et al. | |
| 2008/0319464 A1 | 12/2008 | Bischoff et al. | |
| 2009/0318906 A1 | 12/2009 | König et al. | |
| 2010/0163540 A1 | 7/2010 | Vogel et al. | |
| 2010/0331830 A1 | 12/2010 | Bischoff et al. | |
| 2010/0331831 A1 | 12/2010 | Bischoff et al. | |
| 2011/0224658 A1 | 9/2011 | Bischoff et al. | |
| 2011/0251601 A1 * | 10/2011 | Bissmann | A61F 9/00831 606/5 |
| 2012/0078240 A1 | 3/2012 | Spooner | |
| 2014/0052113 A1 | 2/2014 | Kuehnert et al. | |
| 2014/0088574 A1 | 3/2014 | Bergt et al. | |
| 2014/0288539 A1 | 9/2014 | Bischoff et al. | |
| 2015/0025510 A1 * | 1/2015 | Vogler | A61F 9/00825 606/4 |
| 2015/0164689 A1 | 6/2015 | Vogel et al. | |

FOREIGN PATENT DOCUMENTS

| | | |
|---|---|---|
| DE | 10 2008 062 658 A1 | 6/2010 |
| DE | 10 2013 106 920 A1 | 5/2014 |
| EP | 1 628 606 B1 | 7/2011 |
| WO | WO 03/059563 A2 | 7/2003 |
| WO | WO 2004/105660 A1 | 12/2004 |
| WO | WO 2004/105661 A1 | 12/2004 |
| WO | WO 2005/011547 A1 | 2/2005 |
| WO | WO 2008/055697 A1 | 5/2008 |
| WO | WO 2008/055698 A1 | 5/2008 |
| WO | WO 2008/055705 A1 | 5/2008 |
| WO | WO 2008/055706 A1 | 5/2008 |
| WO | WO 2008/131878 A1 | 11/2008 |
| WO | WO 2009/059711 A1 | 5/2009 |
| WO | WO 2009/059730 A1 | 5/2009 |
| WO | WO 2013/057175 A1 | 4/2013 |

OTHER PUBLICATIONS

König, Karsten, et al., "Intratissue surgery with 80 MHz nanojoule Femtosecond laser pulses in the near infrared," *Optics Express*, vol. 10, No. 3, pp. 171-176 (Feb. 11, 2002).

"Integrierte Femtosekundenlaser-Technologie zur therapeutischen Anwendung Cornealer Chirugie (Integrated Femtosecond Laser Technology for Therapeutic Application of Corneal Surgery)," *Medical Valley*, 2 pgs., Jul. 1, 2010-Jun. 30, 2014.

Simon, Peter, et al., "UV-Femtosekundenlaser und deren anspruchvolle Anwendungen (UV femtosecond lasers and their sophisticated applications)," *Laser Magazin*, pp. 19-21 (Jan. 2011).

Laser keratomer of Ziemer Ophthalmic Systems AG, Port Switzerland (brochure), 3 pgs. (2012).

Laser keratome of Intralase Inc., USA (now Abbott Laboratories, Illinois, USA (brochure), 5 pgs. (2013).

Femtosecond laser keratome "VisuMax" of Carl Zeiss Meditec AG (brochure), 7 pgs. (2015).

* cited by examiner

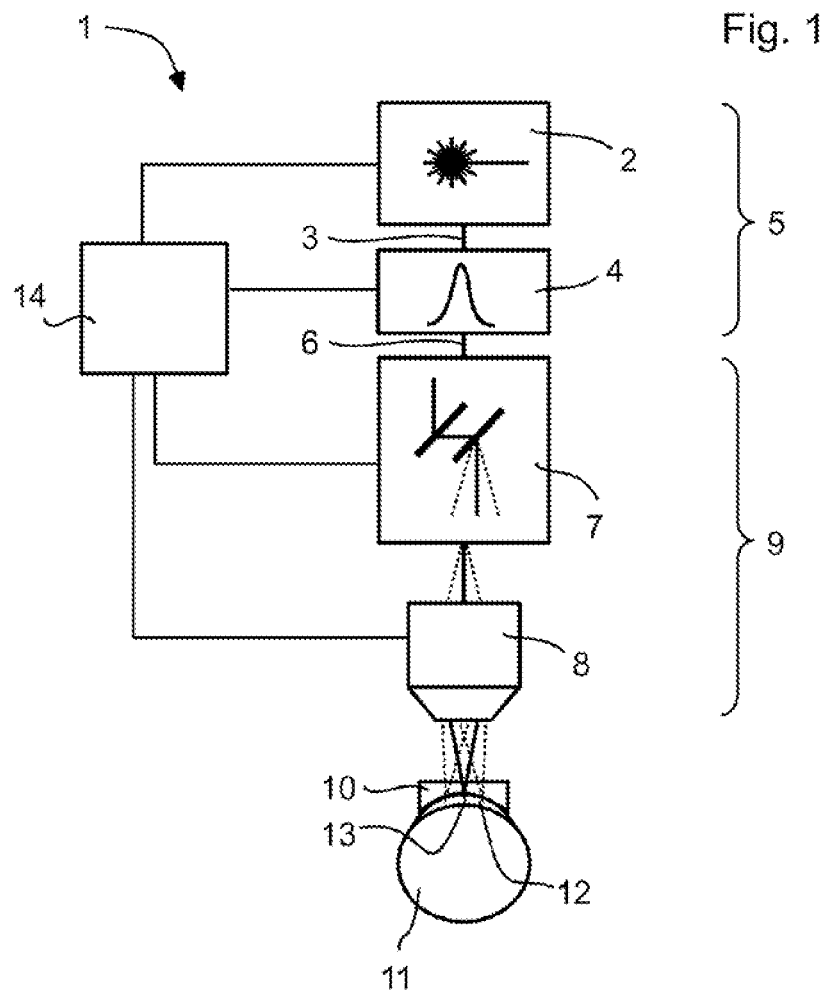
Fig. 1
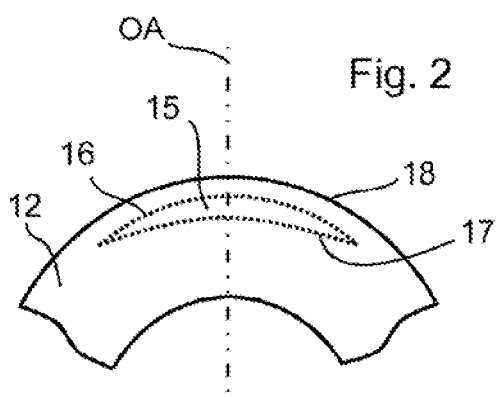
Fig. 2
Fig. 3

CREATION OF CURVED CUTS IN THE INSIDE OF THE EYE CORNEA

PRIORITY CLAIM

The present application is a continuation of U.S. patent application Ser. No. 17/037,441, filed Sep. 29, 2020, which is a continuation of U.S. patent application Ser. No. 14/774,677, filed Sep. 10, 2015, now U.S. Pat. No. 10,893,979, issued Jan. 19, 2021, which is a National Phase entry of PCT Application No. PCT/EP2014/052167, filed Feb. 4, 2014, which claims priority from German Patent Application Number 10 2013 204 496.8, filed Mar. 14, 2013, the disclosures of which are hereby incorporated by reference herein in their entirety.

FIELD OF THE INVENTION

The invention relates to a device for isolating a lenticle in the cornea of an eye, which device has a laser beam source which is designed to emit pulsed laser radiation with a wavelength which penetrates into the cornea, a beam forming unit which has beam optics which bundle the pulsed laser radiation in the cornea into a focus, and a beam deflection unit, which shifts a focus of the radiation in the cornea, wherein a control unit is provided which is designed to control the laser beam source and the beam forming unit, in order to isolate the lenticle in the cornea, which lenticle is delimited by a cut surface.

The invention also relates to a method for isolating a lenticle in the cornea of an eye, wherein at least one cut surface is established in the cornea, which surface defines the lenticle and the cut surface in the cornea is created by emitting pulsed laser radiation, wherein pulsed laser radiation which has a wavelength which penetrates into the cornea is used, and a focus of the laser radiation is shifted in the cornea.

BACKGROUND OF THE INVENTION

The shape of the front surface of the cornea of an eye is important for the imaging properties of the eye. Therefore, it has long been known to use the cornea of an eye to correct impaired vision, with the aim of modifying the front surface of the cornea of an eye and thus its refractive properties and in this way compensate for impaired vision. In the state of the art, surgical procedures which loosen a lamella in the cornea of an eye, fold this lamella back and then remove material from the inside of the cornea of an eye which has been exposed as a result, have been developed for this purpose. Subsequently, the lamella is folded back into place, leaving the cornea of an eye with a differently shaped front surface, due to the removal of material. In the state of the art, this correction method is abbreviated inter alia to LASIK; hereinafter it will be identified as lamella-releasing correction of impaired vision. In earlier embodiments, the lamella was loosened by means of a mechanical keratome. The cornea of an eye was pushed flat by a flat contact lens and the lamella cut by means of the mechanical keratome. In a development, so-called laser keratomes have started to be used by now. Inter alia a laser keratome from Ziemer Ophthalmic Systems AG, Port, Switzerland, is known for this purpose. With regard to its beam deflection, it was designed to create the lamella to be folded back. A further laser keratome was developed by Intralase Inc., USA, which by now is owned by Abbott Laboratories, Illinois, USA. Both laser keratomes work by means of pulsed laser radiation, wherein repetition rates and pulse energies differ.

Surgical correction of impaired vision has been further developed to methods which isolate and extract material in the cornea. The material usually has the form of a lenticle, which is why these methods are called lenticle-extracting methods or devices here. Also, for reasons of clarity, the volume to be isolated and extracted is identified as a "lenticle", even if in specific applications a non-lenticle-shaped volume is to be isolated and extracted.

The devices and methods named at the outset relate to the method of lenticle extraction. Lenticle-extracting devices and methods have the advantage that the front surface of the cornea is damaged in a very much smaller area. It is no longer necessary to have an almost completely annular incision into the front surface of the cornea, as is required for releasing a lamella which would expose the inside of the cornea. Instead, a smaller incision at the edge, which leads to the isolated volume, and through which the isolated volume can be removed, is enough, optionally after reduction of the isolated material. The method of lenticle extraction requires that the cut surfaces isolating the lenticle be created with high precision in the inside of the cornea. In order to correct impaired vision, so as to use as little tissue as possible, additionally at least one of the cut surfaces delimiting the lenticle should lie at a non-uniform distance from the front surface of the cornea. Also here there is a difference from the approach which loosens and folds back a lamella of the cornea, as there the only lamella-creating cut surface may lie at a uniform distance from the front surface of the cornea, thus parallel to the front surface of the cornea. If the front surface of the cornea is pressed flat with a flat contact lens, when creating the cut in the lamella, only one cut surface, which lies parallel to the surface of the contact lens as far as the edge sections, and for its part is also flat, needs to be created.

Lenticle-extracting correction of impaired vision is basically described in WO 2004/105660 and WO 2004/105661. Additionally, developments are known in the state of the art. Thus WO 2005/011547 discloses the use of contour lines for rapid isolation of lenticles, while WO 2008/055697 indicates calculation rules for how the boundary surfaces of the lenticle, i.e., the cut surfaces being created, can be chosen. It is known in particular from this document to divide the cut surfaces delimiting the lenticle into an anterior flap surface which is at a uniform distance from the front surface of the cornea of an eye and a posterior lenticle surface which is not at a uniform distance from the front surface of the cornea. The distance between the surfaces, and thus their shape, influences the curvature of the cornea after correction.

WO 2008/055705 and WO 2008/055706 deal with the issue of curvature of the image field when using a non-planar contact lens and creating control data for the surgical procedure.

The cut surface is usually created by pulsed laser radiation. For this, the targets of the laser radiation are arranged along a path which lies in the cut surface and ultimately specifies the cut surface. WO 2008/055698 outlines the arrangement of targets along the path, wherein it is provided not to specify a target for every pulse of laser radiation emitted into the cornea of an eye.

WO 2008/131878 discusses the question of how, if laser surgery is interrupted, further treatment can take place which takes into consideration changes to the tissue of the cornea which have already been created.

WO 2009/059711 and WO 2009/059730 deal with different profiles of the lenticle to be removed for specific corrections of impaired vision, specifically correcting hyperopia, and specify minimum values for the lenticle.

WO 2003/059563 discloses operating parameters for a laser device for operations to correct impaired vision by means of lenticle extraction. The same applies to EP 1628606 B1.

In the state of the art, the femtosecond laser keratome VisuMax from Carl Zeiss Meditec AG is known for the lenticle-extracting method. It uses a femtosecond fibre laser which emits in the infrared spectral range and which emits at a pulse repetition rate of 500 kHz laser pulses which are focused in the cornea of an eye.

The time it takes to create a cut surface is of great importance both for the quality of the correction of impaired vision and also for acceptance by patients. The longer the duration of the intervention, the greater the risk of disruptive eye movements which reduce the precision of the creation of the cut surface or can even lead to it no longer being possible to create any coherent cut surfaces, and the procedure needing to be interrupted. Also, a longer-lasting intervention places unwanted stress on the patient.

With lamella-releasing correction of impaired vision, the quality of the optical correction is determined essentially by the precision of the volume removed after releasing the lamella. The position of the lamella-releasing cut surface itself is of less, or even no, importance. On the contrary, the exact positioning of the cut surfaces in the cornea of an eye is of great importance for the quality of the result of a lenticle-extracting correction of vision. As the cut surface is created by adjusting the focus of the pulsed laser radiation along a path, ultimately the positioning accuracy of the focus in the cornea of an eye is important. Here, it must not be forgotten that this is a living tissue, which can occasionally be modified during intervention and also does not necessarily react in linear fashion to changes in parameters.

SUMMARY OF THE INVENTION

Therefore, the object of the invention is to develop a device of the type named at the outset or a method of the type named at the outside such that a quick creation of a cut surface with simultaneously high precision can thus be achieved.

This object is achieved, according to the invention, by a device for isolating a lenticle in the cornea of an eye, which has:
  a laser beam source that is designed to emit pulsed laser radiation with
    a pulse frequency of 1.2 MHz to 10 MHz,
    a pulse energy of 1 nJ to 200 nJ, and
    a wavelength which penetrates into the cornea;
  a beam forming unit which has
    beam optics, which have an image field and which bundle the pulsed laser radiation in the cornea into a focus which is located inside the image field and which has a maximum diameter of less than 3 µm, and
    a beam deflection unit which shifts the focus in the cornea and inside the image field, wherein the focus moves along a path while the image field is resting; and
  a control unit, which is designed to control the laser beam source and the beam forming unit, in order to isolate the lenticle in the cornea by specifying the path, which lenticle is delimited by at least one cut surface which is curved with regard to a front surface of the cornea.

The object is further achieved by a method for isolating a lenticle in the cornea of an eye, wherein
  at least one cut surface is established in the cornea, which surface defines the lenticle and is curved with regard to a front surface of the cornea;
    a path which lies in the cut surface is established;
    there is emitted into the cornea pulsed laser radiation with
      a pulse frequency of 1.2 MHz to 10 MHz,
      a pulse energy of 1 nJ to 200 nJ, and
      a wavelength which penetrates into the cornea;
    beam optics are used, which optics have an image field and which bundle the pulsed laser radiation in the cornea into a focus which is located inside the image field and which has a maximum diameter of less than 3 µm; and
    the focus in the cornea and inside the image field is shifted, wherein the focus moves along a path while the image field is resting.

The invention combines different features which together make possible the creation of a cut surface which is curved with regard to the front surface of the cornea. It is not thus a conventional lamella-releasing cut surface, but a cut surface which has no uniform distance from the front surface of the cornea in relation to a cut plane through the eye which contains the axis of vision or the optical axis of the eye. With regard to the front surface of the cornea of the eye the invention provides the curvature, more precisely a two-dimensional curvature, to exist in a central area about the optical axis or the axis of vision of the eye which area for example has a diameter of not more than 10 mm. This is the area which is essential for optical correction, and in this area, customary initial laser cuts of lamella-releasing correction methods have a uniform distance between the front surface of the cornea of an eye and the cut surface, which causes the lamella to expose the inside of the cornea of an eye.

For the following reasons, the combination according to the invention goes beyond a simple aggregation of features and achieves a combined effect:

The individual laser pulses which form the cut surface along the path act differently in the cornea of an eye, depending on pulse energy, pulse frequency and focus diameter. With regard to the separation of tissue due to pulsed laser radiation, two different ways of working can be identified. These different processes will be called "tissue splitting" and "tissue cutting" hereinafter.

If laser pulses are focused into the cornea under specific conditions, in the focal volume there is tissue dissolution which releases gases which are at high pressure and thus exert mechanical forces on the area surrounding the tissue. The corneal tissue consists of a lamellar collagen structure, with the result that, to the best of the inventor's knowledge, the mechanical forces create microruptures which travel along the lamellae. Thus, in addition to the primary process of tissue dissolution in the focal volume, there is a secondary effect which leads to tissue splitting along the collagen structure. If, on the other hand, comparatively small pulse energies and higher repetition rates are being used, there is no secondary effect of tissue splitting, but merely the tissue dissolution created in the volume of the focus causes the separation. The corneal tissue is thus cut, largely regardless of the collagen structure.

The inventors recognized that there is no abrupt transition between tissue splitting and tissue cutting. In the parameter space of the laser pulse application there is a transition region in which either one mechanism or the other plays a more or less substantial role in the process of tissue separation. Furthermore, it has been shown that in lenticle-extraction methods and devices thus far in clinical practice exclusively utilize parameter sets which led to the secondary effect of tissue splitting having a substantial role to play in the separation process. Exclusively tissue-cutting sets of parameters are currently used in clinical practice only by the laser keratome of Ziemer Ophthalmic Systems AG, Port, Switzerland. However, to the best of public knowledge, this device is not capable of creating cut surfaces which are curved with regard to the front surface of the cornea, and, as already stated at the outset, such way of working does not offer any substantial advantage for applications using the lamella-releasing method, and is therefore not important.

It should be emphasised that different ways of working, i.e., the influence of parameters on the question of whether tissue splitting or tissue cutting prevails when creating lenticles, have been identified for the first time by the inventors. The difference between the ways of working with this method is not mentioned in the state of the art. Also, the literature does not assign the individual realisations of the state of the art to these ways of working.

From their work, the inventors recognized also that, with regard to the precision to be achieved, there is a substantial difference between tissue splitting on the one hand, and tissue cutting on the other, only if curved cuts are made. This is because tissue splitting generally always proceeds along the lamellae of the collagen structure of the corneal tissue. With lamellar cuts there is therefore no advantage or disadvantage between lamellar splitting and lamellar cutting in the machining result. For curved cut surfaces it is different: This is because it is not possible, because of the physiologically given lamellae thickness and structure, to place a curved cut surface with high contour accuracy at just any point in the cornea of an eye if tissue-splitting separation is taking place.

The mechanism of tissue cutting allows a very much more precise cut surface positioning and in particular a higher contour accuracy to be achieved. The inventors trace this back to the fact that, in a tissue-cutting process other than tissue splitting, the cut surface does not necessarily follows in boundary surfaces between lamellae of the collagen structure of the corneal tissue, but also can be arranged within a lamella. An advancing fissure (advancing the splitting before the proceeding sequence of laser pulses) which would occur in the lamella plane during tissue splitting is prevented and the separation takes place precisely in the focus position. However, tissue splitting can also be understood as a sort of digitisation of the cut surface position, wherein the smallest unit is the thickness of the lamella as a tissue-splitting created cut surface tends always to lie in boundary surfaces between individual lamellae of the corneal tissue. This is not a defect for cuts which are effected at a uniform distance from the front side of the cornea, because the lamella structure follows the front side of the cornea with good accuracy. For curved cut surfaces of the lenticle, the distance of which from the front side of the cornea varies depending on radius and optionally angle, this type of creation of a cut surface proves disadvantageous.

With regard to pulse frequency, pulse energy and focus diameter, these relationships lead, particularly reliably, to the parameter range according to the invention having a tissue separation in which the process of tissue cutting strongly prevails. The combination with the creation of a cut surface which is curved with regard to the front surface of the cornea and thus does not necessarily follow the boundary surface between lamellae of the collagen structure of the corneal tissue (which otherwise travels largely parallel to the front surface of the cornea) therefore leads to a particularly accurate cut surface positioning and high contour accuracy. In the working range according to the invention, the contribution of tissue splitting is reduced in favor of the effect of tissue cutting, and therefore the cut surface and thus the isolation of the lenticle follow the specified values more precisely for lenticle extraction.

The tissue cutting effect is particularly great if the pulse energy is less than 100 nJ and, particularly preferably, less than 10 nJ. A pulse energy range of 10 nJ to 80 nJ has proved particularly favorable. The same applies for the pulse length of the pulsed laser radiation which, at infrared wavelengths, should be no more than 1 ps.

The wavelength of the laser radiation used is such that the laser radiation can penetrate into the cornea of an eye (transmission factor ≥0.8) and there leads to tissue separation in the inside of the cornea, by means of non-linear effects. For this, a wavelength of 1030-1060 nm has proven useful. Alternatively, laser radiation in the ultraviolet spectral range between 300 nm and 400 nm can be used. It actually tends towards a higher linear interaction fraction (absorption) than the named infrared radiation, but is likewise suitable if the focus diameter does not exceed 2 µm and the pulse frequency is not more than 2 MHz. If laser pulses from this ultraviolet wavelength range are used, pulse lengths of a few ns can also be used effectively.

The lenticle is isolated by the focus being shifted within the image field of the beam optics used and the image field being resting with regard to the cornea to be machined. This is where it differs from the laser keratome of Ziemer Ophthalmic Systems AG, in which a microscope object is used, the image field of which is much too small to achieve complete detection of the area in the cornea to be machined. The microscope object and thus the image field is therefore shifted with this laser keratome. A curved cut surface thus cannot be created with justifiable expense, which is why this laser keratome pushes the front surface of the cornea of an eye flat by means of a planar contact lens, and therefore the created cut surface automatically lies parallel to the front surface of the cornea of an eye. However, the invention uses an resting image field, for which, with regard to the area to be machined, a diameter of at least 3 mm, preferably at least 6 mm and particularly preferably at least 7 mm, is sensible. Small image fields hinder the creation of cut surfaces or are too small for customary lenticles to be isolated.

As the surface is cut by shifting the focus within the image field along a path which lies in the cut surface, almost any curved cut surface in the cornea of an eye can be created with a suitable three-dimensional adjustment of the focal position. Therefore, it is no longer necessary to flatten the cornea of an eye. Instead, work can be done on a curved contact lens, wherein it is preferable that a contact surface of this contact lens to be placed on the front surface of the cornea has a radius of curvature of not more than 50 mm, preferably not more than 20 mm. The curvature of the contact surface of the contact lens specifies the curvature of the cornea during intervention.

To create the curved cut surface, it is also advantageous if the beam optics have an objective with a numerical aperture of at least 0.33 in the cornea.

It is understood that the features mentioned above and those yet to be explained in the following are applicable, not only in the stated combinations, but also in other combinations or singly, without departure from the scope of the present invention.

In particular, the invention can advantageously be used in slightly modified form also for the creation of curved cuts in other elements of the eye, for example in the lens or the vitreous body.

BRIEF DESCRIPTION OF THE FIGURES

The invention is explained by way of example in yet greater detail in the following with reference to the attached drawings, which also disclose features essential to the invention. There are shown in:

FIG. 1 a schematic representation of a device for carrying out a lenticle-extraction correction of impaired vision, FIG. 2 a simplified sectional representation through the cornea of an eye to illustrate the lenticle to be isolated and extracted, and FIG. 3 a projection of a cut surface delimiting the lenticle, to illustrate the creation of the cut surface.

DETAILED DESCRIPTION

FIG. 1 shows, schematically, a device 1 for carrying out a lenticle-extracting correction of impaired vision. Device 1 has a laser 2 which provides pulsed laser radiation, wherein in the embodiment outlined, the laser 2 emits a pulsed pure beam 3 which has a wavelength which penetrates into the tissue of the cornea of an eye, with the result that a machining by means of non-linear effects can take place there. Pure beam 3 is shaped by a chopper 4 with regard to pulse duration, wherein predistortion known from the state of the art can take place, which ensures that the desired pulse length of for example ≤1 ps is present after passing through the further optical path of the beam path in the material, i.e., in the cornea of an eye. Chopper 4 and laser 2 form a laser beam source 5 which emits a pulsed laser beam 6 of the desired pulse length.

Pulsed laser beam 6 also passes through a scanner 7 which preferably brings about a two-dimensional deflection transverse to the direction of propagation of the laser radiation. The laser beam 6 scanned in this way is focused into the cornea of an eye by an objective 8. Scanner 7 forms a beam forming unit 9 together with the objective 8, which ensures that pulsed laser radiation 6 is focused into a cornea of an eye in locations which can be set, wherein the focus diameter there is less than 3 μm.

Laser beam source 5 can optionally comprise a so-called pulse picker which can for example be part of the chopper 4. This pulse picker changes the frequency of the laser radiation pulses in the pure beam 3, which pulses have a machining effect on the cornea of an eye. Thus for example it is possible to design the laser 2 such that it provides a pure beam 3 with a pulse frequency which is clearly higher than that pulse frequency which is desired for the machining-effective laser pulses of the laser beam 6. Then, the pulse picker reduces the frequency of the effective laser radiation pulses by rendering the machining effect of individual laser radiation pulses harmless. This can for example take place by the pulse picker increasing the pulse length. The importance of the pulse picker known in the state of the art will be explained later on with the help of FIG. 3.

In the embodiment shown in FIG. 1, the pulse frequency of the pulsed laser beam 6 is between 1.2 MHz and 10 MHz, wherein the frequency is relative to those pulses which have a machining effect, i.e., pulses which are not rendered harmless by a pulse picker if present.

The energy of these pulses of the pulsed laser beam 6 is between 1 nJ and 200 nJ, preferably between 10 nJ and 100 nJ, particularly preferably between 20 nJ and 80 nJ.

The wavelength of laser beam 6 lies in a range of 1030 nm to 1060 nm or 300 nm to 400 nm or another spectral range which can penetrate into the cornea, for which the cornea thus has a transmission factor of at least 0.8.

Device 1 also comprises a contact lens 10 which serves to fix the eye 11 and also to give the front surface of the cornea 12 of an eye 11 a desired and known shape. The corresponding contact surface of contact lens 10 has a radius of curvature of 50 mm or less, particularly preferably 20 mm or less, for this purpose.

Objective 8 bundles the laser radiation 6 into a focus 13 which is inside the cornea 12. Focus 13 has a maximum diameter of 3 μm, preferably a maximum of 2 μm. The maximum diameter is the largest diameter which, e.g., in the event of an elliptical focus spot, is measured along the large semiaxis. In the event of a circular spot, the spot diameter is the relevant measurement.

The dotted line of FIG. 1 shows that, depending on the effect of the scanner 7, the focus 13 is at different points in the cornea 12 of an eye 11. In the design of FIG. 1, the scanner 7 brings about a deflection transverse to the main direction of incidence of the laser radiation 6. The focus position is adjusted along the main direction of incidence by suitable actuation of the objective 8, which is designed to be suited to a z-adjustment.

The laser beam source 5 (in the design of FIG. 1 produced by laser 2 and chopper 4) as well as the beam forming unit 9 (in the design of FIG. 1 produced by scanner 7 and objective 8) are connected to a control apparatus 14 via control lines, not shown in more detail, which control apparatus controls these elements in suitable manner. The actuating of the control apparatus 14 creates a cut surface in the cornea of an eye. The corresponding relationships are represented in a sectional representation in FIG. 2, which shows the cornea 12 schematically.

A lenticle 15 in the cornea 12 is isolated by adjusting the focus 13 of the pulsed laser radiation 6. Lenticle 15 is delimited at the front by a flap surface 16 and at the back by a lenticle surface 17. In order to be able to keep the boundary surfaces of the lenticle 15 as simple as possible, the flap surface 16 is at a uniform distance from the front surface 18 of cornea 12. Flap surface 16 is thus not curved with regard to front surface 18. This is different in lenticle surface 17 which is curved with regard to the front surface 18. Without such a curvature, the removal of the lenticle 15 would not change the curvature of the front surface 18 of the cornea 12. If the lenticle 15 is removed, however, the lenticle surface 17, curved with regard to front surface 18, changes the curvature of the front surface 18 of the cornea 12. This is removed by a lateral cut, not shown in FIG. 2, which cut for example leads at the edge of lenticle 15 from the flap surface 16 to the front surface 18 and makes it possible for the isolated lenticle 15 to be extracted, optionally after reduction of the material of the lenticle 15. In the representation of FIG. 2, flap surface 16 and lenticle surface 17 are symmetrical to the optical axis OA. This is set automatically for flap surface 16 if it has a uniform distance from front surface 18.

The boundary surfaces of the lenticle 15 may naturally also comprise further surfaces apart from flap surface 16 and lenticle surface 17. For example, with a lenticle 15 which is thinner on the optical axis OA than in regions far away from the axis, an additional edge surface can be provided which connects flap surface 16 to lenticle surface 17, which then has a more curved path than flap surface 16 and front surface 18.

The cut surfaces for isolating the lenticle 15 are thereby created by the focus 13 being shifted along a path which lies in the corresponding surface. This is shown by way of example in FIG. 3 with the help of lenticle surface 17 which, for reasons of clarity, is elliptical here. This is intended to show that device 1 can be used to correct not only a spherical visual defect but also an astigmatism. Basically, during higher-aberration corrections, lenticle 15 is no longer rotation-symmetrical to the optical axis OA. FIG. 3 shows a folding-up of the lenticle surface 17 in the drawing plane. In FIG. 3, a path 19 is drawn in using a dotted line. The position of the focus 13 is adjusted along this path. Generally, naturally not just one adjustment transverse to the optical axis OA is necessary, but also an adjustment of the focus position along the optical axis OA. This therefore cannot be seen in FIG. 3, as this figure shows a folding-up of the lenticle surface 17 in the drawing plane, which is why, in the representation of FIG. 3, path 19 lies in a plane. By looking at the cut through lenticle 15 in FIG. 2 it becomes clear that, the greater the distance from the optical axis OA, the further away from the front surface 18 the z-position of the focus is shifted.

Targets 20 are drawn in along the path 19 of FIG. 3. In each case they indicate a point at which a laser pulse of the pulsed laser radiation 6 is emitted. The lenticle surface 17 is designed as a cut surface overall by arranging the targets 20 in series along the path 19 and by a suitable choice of the path 19. The distances between targets 20 are chosen such that the fewest possible material bridges remain, meaning that the lenticle surface 17 is thus generated entirely as a cut surface.

With the help of FIG. 3 it can easily be understood why it is advantageous to make it possible to change the pulse frequency of the pulsed laser beam 6. If it were desired to arrange the targets 20 to be as equidistant as possible, the pulse frequency and the shift speed of the beam forming unit 9 can be adapted to one another. As a high pulse frequency laser 2 can generally be adjusted only at great expense, it is advantageous to provide firstly a pure beam 3 with the laser 2, which pure beam has a pulse frequency which is greater than or equal to the maximum pulse frequency desired for the laser beam 6. It may be easier to produce such a laser 2 and to combine same with a pulse picker than to design a laser with a pulse frequency which can be directly adjusted. Thus the pulse frequency can be adapted to the shift speed, and the time taken to create cut surfaces is reduced.

The parameters for pulse energy, pulse frequency, focus diameter and optionally pulse length, named in the description of the figures as well as in the general part of the description, lead to the cut surfaces being created with a mechanism for separating tissue which uses tissue cutting and essentially tissue splitting to their full capacity. Thus a desired position for the delimiting cut surfaces of the lenticle 15 can be produced with great precision.

What is claimed is:

1. A device for generating a cut in an interior of an eye, the device comprising:
    a contact lens comprising a contact surface for placing on a cornea of the eye;
    a laser beam source designed to emit laser radiation having a pulse frequency of at least 1.2 MHz and a wavelength which penetrates the cornea, wherein the energy of each individual pulse separating tissue within the cornea having a pulse energy of 10 nJ to 80 nJ;
    beam optics designed to focus the laser radiation through the contact lens into a focus located in the eye;
    a beam scanner designed to shift the focus in the eye along a path within the cornea to generate the cut as a cut which confines a lenticule within the cornea, wherein the cut is, at least in parts, curved against a frontside or backside of the cornea; and
    a processor, which is connected with the beam scanner and is designed to control the beam scanner by specifying the path and thus defining location and extension of the cut confining the lenticule within the cornea;
    wherein the laser beam source is configured to minimize tissue-splitting separation of collagen structures of the corneal tissue, thereby improving contour accuracy of the curved cut surface and of dimensions of the isolated lenticule.

2. The device according to claim 1, wherein the pulse frequency is not more than 10 MHz.

3. The device according to claim 1, wherein the laser beam source is designed to emit the laser radiation pulses having a wavelength of 1030 nm to 1060 nm.

4. The device according to claim 1, wherein the laser beam source is designed to emit the laser radiation pulses having a wavelength of 300 nm to 400 nm.

5. The device according to claim 1, wherein the laser beam source is designed to emit the laser radiation pulses having a pulse length of less than 1 ps.

6. The device according to claim 1, wherein the focus has a maximum diameter of less than or equal to 3 μm.

7. The device of claim 1, wherein the contact surface has a radius of curvature of not more than 50 mm.

8. The device according to claim 1, wherein
    the laser beam source is configured to emit the laser radiation as a raw train of laser radiation pulses having the pulse frequency of at least 1.2 MHz and the wavelength which penetrates the cornea, wherein each laser radiation pulse of the raw train has a pulse length and a pulse energy sufficient to separate layers of material at the focus within the eye;
    the device further comprises a pulse picker which selects some laser radiation pulses of the raw train to provide a modified train of laser radiation pulses, wherein each laser radiation pulse of the modified train of laser radiation pulses has a pulse length and a pulse energy sufficient to separate layers of material within the eye, the modified train having a pulse frequency reduced over the raw pulse frequency; and
    wherein the beam scanner shifts the focus in the eye to generate the cut as a cut within the cornea by the modified train of laser radiation pulses emitted while the focus is shifted.

9. The device according to claim 8, wherein the beam optics comprise an optical field with a diameter of 6 mm or larger.

10. The device according to claim 1, wherein the beam optics comprise an optical field with a diameter of 3 mm or larger.

11. The device according to claim 1, wherein the beam optics comprise an optical field and the beam scanner shifts the focus within the optical field while the optical field is resting in the eye.

12. The device according to claim 1, wherein the beam optics comprise an optical field and the beam scanner shifts the focus within the optical field while the optical field is resting in the eye.

13. A method for generating a cut in an interior of an eye, the method comprising:

providing a contact lens comprising a contact surface and placing the contact surface on the cornea;

emitting laser radiation pulses having a pulse frequency of at least 1.2 MHz and a wavelength which penetrates a cornea of the eye;

focusing the laser radiation pulses into a focus located in the eye by using beam optics; and shifting the focus in the eye along a path which defines location and extension of the cut as a cut which is within the cornea and confines a lenticule within the cornea, wherein the cut is, at least in parts, curved against a frontside or backside of the cornea;

wherein the energy of each individual pulse separating tissue within the cornea has a pulse energy of 10 nJ to 80 nJ or the beam optics comprises an objective with a numerical aperture of at least 0.33, and wherein the laser beam source and the beam optics are configured to minimize tissue-splitting separation of collagen structures of the corneal tissue, thereby improving contour accuracy of the curved cut surface and of dimensions of the isolated lenticule.

14. The method according to claim 13, wherein the pulse frequency is not more than 10 MHz.

15. The method according to claim 13, wherein the wavelength is between 1030 nm to 1060 nm or between 300 nm to 400 nm.

16. The method according to claim 13, wherein the laser radiation pulses have a pulse length of less than 1 ps.

17. The method according to claim 13, wherein a maximum diameter of the focus is less than or equal to 3 μm.

18. The method according to claim 13, further comprising the following steps:

emitting the laser radiation pulses in a raw train of laser radiation pulses having the raw pulse frequency of at least 1.2 MHz as a raw pulse frequency, wherein each laser radiation pulse of the raw train has a pulse length and a pulse energy sufficient to separate layers of material at a focus within the eye; and selecting some laser radiation pulses of the raw train to provide a modified train of laser radiation pulses, wherein each laser radiation pulse of the modified train of laser radiation pulses has a pulse length and a pulse energy sufficient to separate layers of material within the eye, the modified train having a pulse frequency reduced over the raw pulse frequency;

wherein the steps of focusing and shifting use the modified train of laser radiation pulses.

19. The method according to claim 13, wherein the contact surface has a radius of curvature of not more than 30 mm.

20. A device for generating a cut in the interior of an eye, the device comprising:

a contact lens comprising a contact surface for placing on a cornea of the eye;

a laser beam source designed to emit laser radiation having a pulse frequency of at least 1.2 MHz and a wavelength which penetrates the cornea;

beam optics designed to focus the laser radiation through the contact lens into a focus located in the eye and comprising an objective with a numerical aperture of at least 0.33;

a beam scanner designed to shift the focus in the eye along a path within the cornea to generate the cut as a cut which confines a lenticule within the cornea, wherein the cut is—at least in parts—curved against a frontside or backside of the cornea; and a processor, which is connected with the beam scanner and is designed to control the beam scanner by specifying the path and thus defining location and extension of the cut confining the lenticule within the cornea;

wherein the beam optics are configured to minimize tissue-splitting separation of collagen structures of the corneal tissue, thereby improving contour accuracy of the curved cut surface and of dimensions of the isolated lenticule.

* * * * *